United States Patent [19]
Kohayakawa

[11] Patent Number: 5,231,430
[45] Date of Patent: Jul. 27, 1993

[54] OPHTHALMIC APPARATUS

[75] Inventor: Yoshimi Kohayakawa, Yokohama, Japan

[73] Assignee: Canon Kabushiki Kaisha, Tokyo, Japan

[21] Appl. No.: 738,145

[22] Filed: Jul. 30, 1991

[30] Foreign Application Priority Data

Jul. 31, 1990 [JP] Japan ................... 2-204874
Jul. 31, 1990 [JP] Japan ................... 2-204875
Jul. 19, 1991 [JP] Japan ................... 3-203177

[51] Int. Cl.⁵ .............................. A61B 3/00
[52] U.S. Cl. ..................... 351/243; 351/211; 351/203
[58] Field of Search ............... 351/200, 203, 211, 216, 351/222, 223, 237, 238, 239, 243

[56] References Cited

U.S. PATENT DOCUMENTS 4,929,865  5/1990  Blum .................... 350/276 R

FOREIGN PATENT DOCUMENTS 59-9912   3/1984  Japan .
59-85641  5/1984  Japan .
60-171031 9/1985  Japan .

Primary Examiner—Rodney B. Bovernick
Assistant Examiner—Hung Xuan Dang
Attorney, Agent, or Firm—Fitzpatrick, Cella, Harper & Scinto

[57] ABSTRACT

An ophthalmic apparatus includes a lens having a diameter greater than the distance between the pupils of the eyes of a user to be tested, adapted to be disposed in front of the eyes, a first visual target, including a visual target portion and a surrounding field of view defining portion, disposed at or near a focal plane of the lens, and a light source for illuminating the visual target portion and the surrounding field of view defining portion.

26 Claims, 6 Drawing Sheets

OPHTHALMIC APPARATUS

BACKGROUND OF THE INVENTION

1. Field of the Invention

This invention relates to an ophthalmic apparatus, for example, an optometric visual target apparatus or an ocular refractivity measuring apparatus used in the practice of optometry in an ophthalmic hospital or the like.

2. Description of the Prior Art

A conventional optometric apparatus for measuring ocular refractivity or the like incorporates an optometric visual target device for optically generating a distant-sight visual target. As used in this document, the terms "distant sight visual target" and "visual target for distant sight" refer to a visual target that 1) appears to the viewer to be at an infinite distance from the viewer, 2) appears to the viewer to be at approximately 5-6 m from the viewer, or 3) is actually approximately 5-6 m or further from the viewer. In addition, as used in this document, the term "visual target for near sight" refers to a visual target that appears to the viewer to be approximately 20-30 cm from the viewer or is actually approximately 20-30 cm from the viewer. There have been known, for example, a device which provides a separate visual target for each eye to be tested, as disclosed in Japanese Utility Model Application Publication No. 59-9912 (1984), and a device which provides a visual target using an edge prism, as disclosed in Japanese Patent Application Public Disclosure (Kokai) No. 60-171031 (1985).

The above-described conventional devices, however, have the following problems. In the device which provides a separate visual target for each eye, two visual targets must be provided within the device, and so a wide field of view cannot be obtained. In the device which uses a wedge prism, an aberration due to the wedge prism is produced, distorting an image. In the both devices, the natural visual sensation of the visual target experienced by the user is impaired, and so complete remissive adjustment cannot be performed. Hence, there is the possibility of inducing mechanical myopia, influencing the optometric value.

In a conventional subjective ocular refractivity measurement, a visual target for distant sight is disposed at a far distance of 5 m and a lens is mounted in front of an eye to be tested, and the diopter value of the lens is changed so that the visual target can be recognized. However, such an arrangement takes up a large amount of space. Therefore, various kinds of apparatuses have been devised for the purpose of saving space. These include an apparatus which provides an eye to be tested with a visual target actually disposed near the eye which appears as if the visual target is at a far distance by means of an optical system using a stereoscopic microscope; an apparatus which makes the optical path from a visual target disposed near an eye to be tested to the eye long by using an optical system combining a plurality of mirrors; and an apparatus which provides a collimating lens and a visual target in front of each eye to be tested, each visual target being disposed at the position of the focus of its collimating lens.

The above-described conventional apparatuses, however, have the following disadvantages. In the apparatus using a stereoscopic microscope, since a Maxwellian view is provided, part of the field of view is cut off if the face of the person to be tested moves. In the apparatus which uses an optical system combining a plurality of mirrors, since a large space is occupied by the mirrors within the apparatus, it is difficult to design a large field of view. In the apparatus which provides each eye to be tested with a collimating lens and a visual target, a large field of view cannot be provided. In any of the conventional apparatuses, part of the field of view frequently is cut off or is small during measurement, and therefore, natural visual sensation is not provided, and so complete remissive adjustment cannot be performed, inducing in some cases mechanical myopia. Accordingly, the measured value obtained by such an apparatus differs from the measured value obtained by an ocular refractivity measuring apparatus when a visual target disposed at a far distance of 5 m is actually provided, and hence accuracy in measurement by the conventional apparatus is low, preventing wide distribution of such apparatuses.

An apparatus which provides a visual target using a Maxwellian view has been disclosed, for example, in Japanese Patent Application Public Disclosure (kokai) No. 59-85641 (1984). This approach, however, has the disadvantage that a visual target cannot be observed if the position of an eye moves a little, and so a sufficiently wide field of view cannot be provided.

SUMMARY OF THE INVENTION

It is an object of the present invention to overcome the problems of the prior art.

It is another object of the present invention to provide an optometric visual target apparatus which has a wide field of view and which can provide a visual image appearing to be 5-6 m from the user without distortion or impairing the natural visual sensation experienced by the user when viewing an image 5-6 m away.

It is still another object of the present invention to provide a space-saving ocular refractivity measuring system which can perform subjective ocular refractivity measurements with high accuracy.

The invention which achieves these objectives, according to one aspect, relates to an ophthalmic apparatus comprising a lens, having a diameter greater than the distance between the pupils of the eyes of a user to be tested, adapted to be disposed at a first position in front of the eyes, a first visual target, comprising a visual target portion and a surrounding field of view defining portion, disposed at or near a focal plane of the lens, and illumination means for illuminating the visual target portion and the surrounding field of view defining portion. The lens has an optical power such that visual target means appears to be approximately 5-6 meters from the user.

The first visual target is fixed in the direction of the optical axis of the lens. The lens has an optical axis and comprises a lens portion spaced from the optical axis. The surrounding field of view defining portion has a distant scene image thereon appearing to be approximately the same distance from the user as the visual target portion. The illumination means comprises different light sources for illuminating the visual target portion and the surrounding field of view defining portion.

In one embodiment the lens comprises a single lens. In this embodiment, the single lens further comprises means for retracting the lens away from the first position to a second position out of the optical path of an eye of the user while the first visual target is disposed at or near the focal plane of the lens defined when the lens is in the first position, thereby permitting the performing of a near sight test of the eyes of the user. The first visual target is adapted to be removed from its position at or near a focal plane of the lens when the lens is disposed in front of the eyes of the user in the optical path thereof. The apparatus further comprises a second visual target adapted to be disposed at or near a focal plane of the lens to be used in the near sight test of the eyes of the user when the lens is retracted to the second position. The first and second visual targets have different visual target portions.

In another embodiment, the lens comprises a plurality of lenses. In this embodiment, the apparatus further comprises means for retracting at least one of the plurality of lenses away from the first position to a second position out of the optical path of an eye of the user while the first visual target is disposed at or near the focal plane of the at least one of the plurality of lenses is in the first position, thereby permitting the performing of a near sight test of the eyes of the user. The retracting means can retract another lens, different from the at least one of the plurality of lenses, away from the first position to a second position out of the optical path of an eye of the user while the first visual target is disposed at or near the focal plane of the another lens defined when the another lens is in the first position, thereby permitting the performing of another near sight test of the eyes of the user. The first visual target is adapted to be removed from its position at or near a focal plane of the lens when the lens is disposed in front of the eyes of the user in the optical path thereof. The apparatus further comprises a second visual target adapted to be disposed at or near a focal plane of the lens to be used in the near sight test of the eyes of the user when the lens is retracted to the second position by the retracting means. The first and second visual targets have different visual target portions.

According to another aspect, the present invention relates to two variable diopter subjective ocular refractivity measuring lenses spaced apart and adapted to be disposed in front of the right and left eyes of a user to be tested, a lens having a diameter greater than the distance between the pupils of the eyes of the user to be tested, adapted to be disposed at a first position in front of the two variable-diopter subjective ocular refractivity measuring lenses, a first visual target, comprising a visual target portion and a surrounding field of view defining portion, disposed at or near a focal plane of the lens, and illumination means for illuminating the visual target portion and the surrounding field of view defining portion. The lens has a optical power such that the visual target means appears to be approximately 5-6 meters from the user.

The ophthalmic apparatus further comprises a light beam divider positioned between the two variable-diopters-subjective ocular refractivity measuring lenses and the lens, and an objective ocular refractive power measuring system positioned to receive light from the light beam divider. The objective ocular refractive power measuring system comprises display means for displaying images of the anterior portion of the user's right and left eyes. The ophthalmic apparatus further comprises left-and-right eye direction moving amount detecting means for detecting the distance between the pupils of the eyes of the user according to the images of the anterior portion of the right and left eyes of the user. The two variable-diopter subjective ocular refractivity measuring lenses are displaceable din a direction connecting the right and left eyes of the user in order to adjust the distance between the two variable-diopter subjective ocular refractivity measuring lenses to be equal to the distance between the pupils of the right and left eyes of the user.

The first visual target is fixed in the direction of the optical axis of the lens. The lens has an optical axis and comprises a lens portion spaced from the optical axis. The surrounding field of view defining portion has a distant scene image thereon appearing to be approximately the same distance from the user as the visual target portion. The illumination means comprises different light sources for illuminating the visual target portion and the surrounding field of view defining portion.

In one embodiment the lens comprises a single lens. In this embodiment, the apparatus further comprises means for retracting the lens away from the first position to a second position out of the optical path of an eye of the user while the first visual target is disposed at or near the focal plane of the lens defined when the lens is in the first position, thereby permitting the performing of a near sight test of the eyes of the user. The two variable-diopter-subjective ocular refractivity measuring lenses are displaceable in a direction perpendicular to the optical axis thereof in order to adjust the distance between the two variable-diopter subjective ocular refractivity measuring lenses to be equal to the distance between the pupils of the right and left eyes of the user. The first visual target is adapted to be removed from its position at or near a focal plane of the lens when the lens is disposed in front of the eyes of the user in the optical path thereof. The apparatus further comprises a second visual target adapted to be disposed at or near a focal plane of the lens to be used in the near sight test of the eyes of the user when the lens is retracted to the second position by the retracting means. The first and second visual targets have different visual target portions.

In another embodiment the lens comprises a plurality of lenses. In this embodiment the apparatus further comprises means for retracting at least one of the plurality of lenses away from the first position to a second position out of the optical path of an eye of the user while the first visual target is disposed at or near the focal plane of the at least one of the plurality of lenses defined when the at least one of the plurality of lenses is in the first position, thereby permitting the performing of a near sight test of the eyes of the user. The retracting means retracts another lens, different from the at least one of the plurality of lenses, away from the first position to a second position out of the optical path of an eye of the user while the first visual target is disposed at or near the focal plane of the another lens defined when the another lens is in the first position, thereby permitting the performing of another near sight test of the eyes of the user. The first visual target is adapted to be removed from its position at or near a focal plane of the lens when the lens is disposed in front of the eyes of the user in the optical path thereof. The apparatus further comprises a second visual target adapted to be disposed at or near a focal plane of the lens to be used in the near sight test of the eyes of the user when the lens is retracted to the second position by the retracting means. The first and second visual targets have different visual target portions.

DETAILED DESCRIPTION OF THE PREFERRED EMBODIMENTS

The present invention will now be explained in detail with reference to the preferred embodiments shown in the drawings.

Figure 1:
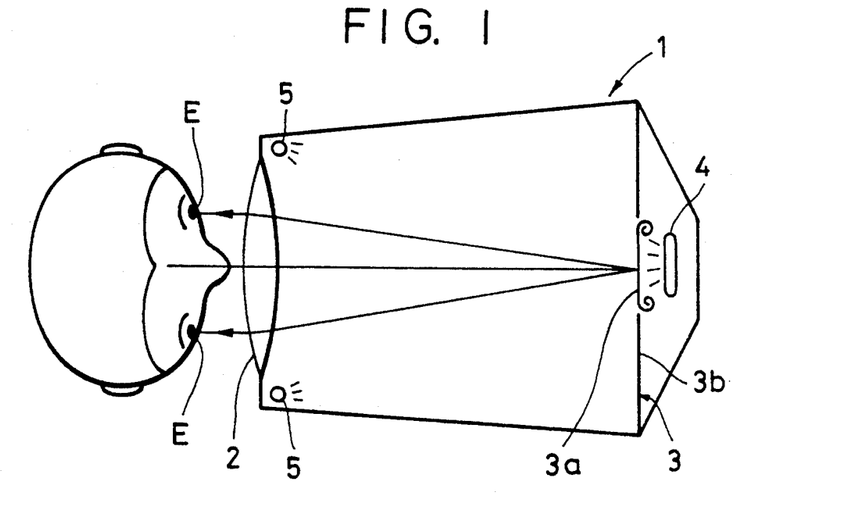
FIG. 1 illustrates a schematic top view of an embodiment of the present invention.

FIG. 1 shows the configuration of an optometric apparatus 1 according to an embodiment of the present invention. In the optometric apparatus 1, a collimating lens 2 having a diameter greater than the pupil distance of the eyes E to be tested is provided facing the eyes E. As shown in the front view of FIG. 2, a wide visual target 3 comprising a central visual target portion 3a having Landholt rings, characters and the like marked on a transparent member, and a surrounding field of view portion 3b made of an opaque material, is disposed at a fixed position spaced from the lens 2 in the direction of the optical axis thereof at or near the focal plane of the collimating lens 2. The wide visual target 3 is much longer than the central visual target portion 3a, the size in each horizontal and vertical direction of the wide visual target 3 being 2 times or more (sometimes 3 times or more) as long as that of the central visual target portion 3a. A light source 4 for illuminating the visual target portion 3a is disposed behind the visual target 3. In order to illuminate the surrounding portion 3b, a plurality of light sources 5 are disposed facing the visual target 3 at a position deviating from the optical axis of the collimating lens 2. As a result, the visual target portion 3a and the surrounding portion 3b are illuminated with the same quantity of light.

Figure 2:
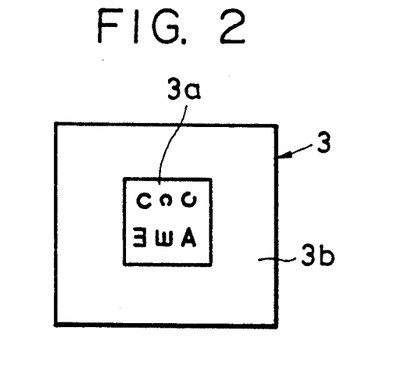
FIG. 2 is a front view of a visual target.

If the light sources 4 and 5 are lit when providing the eyes E with the visual target 3, light beams from the visual target portion 3a become parallel light beams after passing through the collimating lens 2, and reach the eyes E. If the light sources 4 and 5 illuminate the surrounding field of view portion 3b with the same quantity of light as the visual target portion 3a, since the eyes E cannot recognize the boundary between the visual target position 3a and the surrounding field of view portion 3b, and the end portion of the collimating lens 2, the field of view of the eyes E is widened. Hence, the visual target 3 is provided for the eyes E as if it were apparently disposed at a far distance of 5-6 m, and the natural visual sensation of the eyes E is not impaired.

If the area of the visual target portion 3a is too large, there is the possibility that the natural visual sensation of the eyes E is impaired influenced by the abberation of the collimating lens 2 when the eyes E recognize a visual target in the visual target portion 3a. Hence, it is necessary to restrict the area of the visual target portion 3a in accordance with the diameter of the collimating lens 2. It is also within the scope of the invention to remove a portion of the collimating lens 2 as long as the removal does not cause the lens 2 to obstruct the field of view.

Although, in the present embodiment, the visual target portion 3a is illuminated from behind, the visual target portion 3a may be illuminated from the front utilizing light beams from the light sources 5, or it may be illuminated by guiding light beams from an illumination lamp in the room. In order to prevent reflection of light beams from the illumination lamp in the room by the surface of the collimating lens 2, it is desirable to provide a hood for the collimating lens 2.

Figure 3:
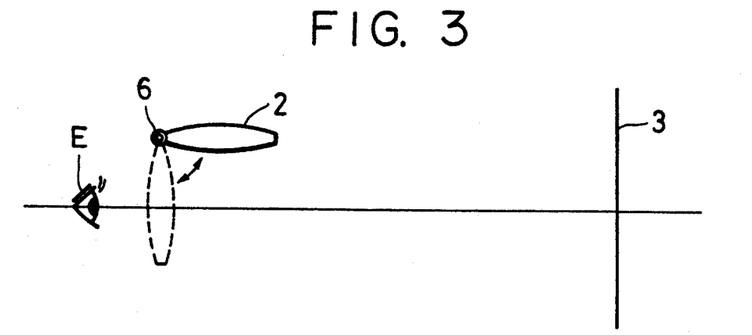
FIG. 3 is a schematic side view illustrating how a collimating lens is retrated out of an optical path.

FIG. 3 illustrates how the collimating lens 2 is retrated out of the optical path along the ocular axis of the eye E from the eye E to the target 3. In FIG. 3, the collimating lens 2 is mounted so as to be rotatable around a shaft 6 in the directions of the arrows, so it can be disposed within the optical path. The other components are the same as in FIG. 1. The visual target 3 is 30-40 cm from the eyes ER and EL.

If the collimating lens 2 is disposed in the optical path as shown by broken lines, it is possible to use the visual target 3 as a visual target for distant sight (so that the visual target 3 appears to be at an infinite distance from the eye E or at a position of 5-6 m from the eyes E), as in the FIG. 1 embodiment. By removing the collimating lens 2 from the optical path as shown by solid lines, it is possible to use the visual target 3 as a visual target for near sight (i.e., a visual target adapted to be viewed at a position of 30-40 cm from the eyes E). The visual target 3 is present in the same plane both in the case of distant sight and in the case of near sight. In addition, different visual targets may be used in the case of distant sight and in the case of near sight, or the same visual target may be use in both cases.

Figure 4:
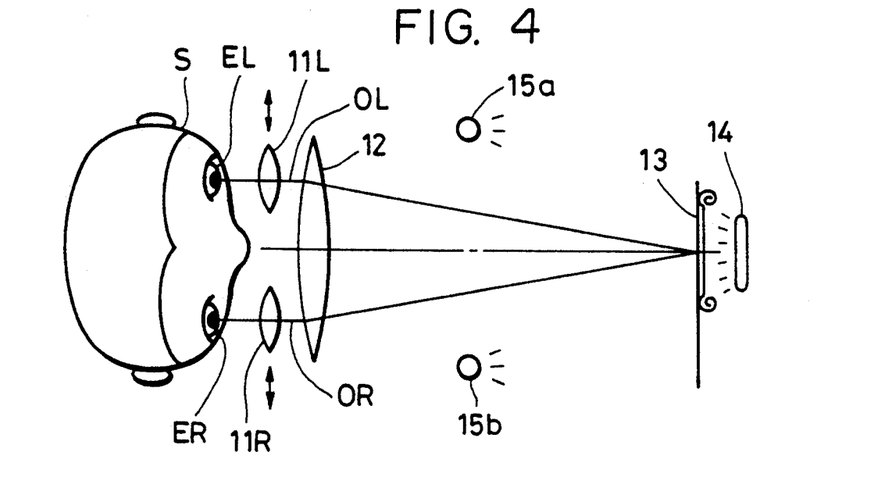
FIG. 4 is a schematic top view illustrating the configuration of an ocular refractivity measuring apparatus according to another embodiment of the present invention.

FIG. 4 illustrates the configuration of an ocular refractivity measuring apparatus according to another embodiment of the present invention. In FIG. 4, lenses 11L and 11R for subjective measurement are disposed in front of left and right eyes EL and ER, on ocular axes OL and OR of the left and right eyes EL and ER, respectively, of a person S to be tested. A collimating lens 12 having a diameter greater than the distance between the pupils of the eyes EL and ER is disposed, in common for the eyes EL and ER, in front of the lenses 11L and 11R. A visual target 13 is disposed at or near the position of the focus of the collimating lens 12. In order to illuminate the visual target 13, a light source 14 is disposed behind the visual target 13. Further, in order to illuminate the neighborhood of the visual target 13, light sources 15a and 15b are disposed in front of the visual target 13.

Figure 5:
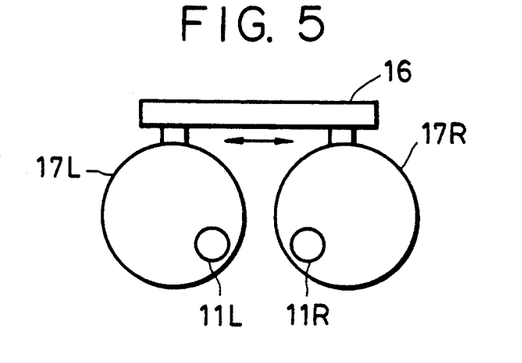
FIG. 5 is a schematic side view illustrating how lenses for subjective measurement are held.

FIG. 5 shows how the lenses 11L and 11R for subjective measurement are held. Two turrets 17L and 17R are mounted on a frame 16 of the ocular refractivity measuring apparatus so as to be movable in the right and left directions. The distance between the lenses 11L and 11R can be adjusted in accordance with the distance between the pupils of the eyes EL and ER. A plurality of lenses 11L and 11R for subjective measurement having different diopter values are mounted on the turrets 17L and 17R, respectively. By being rotated to the positions shown in FIG. 5, each pair of the lenses 11L and 11R for subjective measurement can be selectively inserted on the ocular axes OL and OR, respectively.

When measuring ocular refractivity, the position of the turret 17 is adjusted in accordance with the distance between the pupils of the eyes EL and ER. When the light sources 14, 15a and 15b are lit, light beams from the visual target 13 advance toward the eyes EL and ER, are made to be parallel light beams by the collimating lens 12, pass through the lenses 11L and 11R for subjective measurement, and reach the eyes EL and ER. In this state, the person to be tested selects the lenses 11L and 11R for subjective measurement having different diopter values so that the eyes EL and ER can clearly recognize the visual target 13, to measure the ocular refractivity.

The collimating lens 12 causes light beams from the visual target 3 to appear like light beams from a far distance. If the size of the collimating lens 12 is sufficiently large, nothing restricts the field of view except the lenses 11L and 11R for subjective measurement of ocular refractivity, and the neighborhood of the visual target 13 is also illuminated by the light sources 15a and 15b. Hence, the eyes EL and ER are provided with a wide and light field of view. Accordingly, the field of view is never deficient in producing a natural visual sensation and is never impaired during measurement. As a result, it is possible to perform measurement in a stable state for the eyes EL and ER, and to improve accuracy in measurement. The collimating lens 12 may be cut in such a manner as to not restrict the field of view of the eyes EL and ER.

Figure 6:
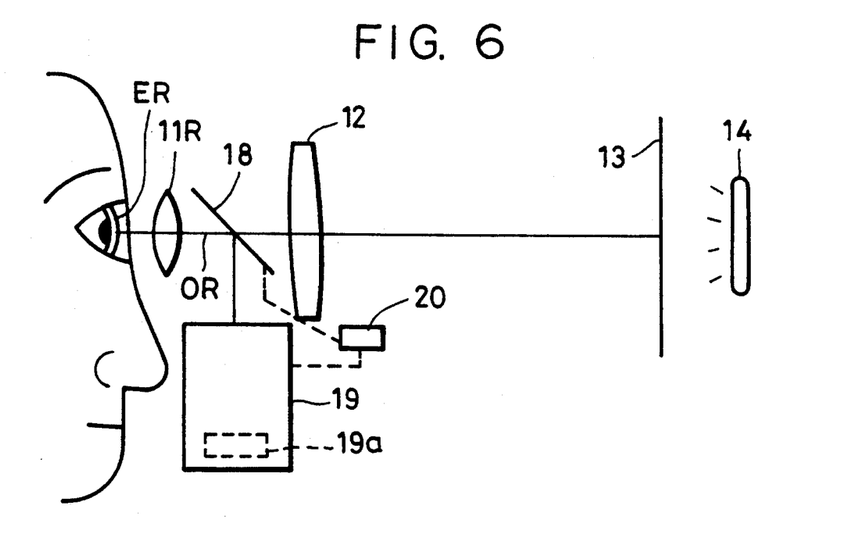
FIG. 6 a schematic side view illustrating still another embodiment of the present invention which includes subjective and objective ocular refractivity measuring systems.

FIG. 6 shows the configuration of a still another embodiment wherein the apparatus of the foregoing embodiment is combined with an objective ocular refractivity measuring apparatus. In FIG. 6, like numerals as those in FIG. 4 indicate like components.

A dichroic mirror 18 having a wavelength dividing characteristic of reflecting infrared light beams and transmitting visible light beams is provided on the ocular axis OR of the eye ER between the lens 11R for subjective measurement of ocular refractivity and the collimating lens 12. An objective ocular refractivity measuring optical system 19 is disposed so as to receive light reflected from the dichroic mirror 18. The dichroic mirror 18 is movable in a direction perpendicular to the ocular axis OR, that is, in a horizontal direction between the left and right eyes, and can be positioned on the ocular axis OL between the lens 11L for subjective measurement and the collimating lens 12 when measuring the left eye EL and on the ocular axis OR between the lens 11R and the collimating lens 12 when measuring the right eye ER. The objective ocular refractivity measuring optical system 19 may be movable together with the dichroic mirror 18 in the horizontal direction between the left and right eyes, or it may be fixedly disposed so as to be able to selectively receive light beams from the left or right eye.

In objective ocular refractivity measurement, infrared light beams issued from the objective ocular refractivity measuring optical system 19 are reflected by the dichroic mirror 18, and reach the eye ER. Light beams reflected by the fundus of the eye ER return along the same optical path, and are guided to the measuring optical system 19, within which an ocular refractivity measurement is performed. The objective ocular refractivity measurement of the eye EL is performed in the same manner by moving the dichroic mirror 18 on the ocular axis OL. The dichroic mirror 18 may have a length of at least the distance between the pupils of the eyes, and is fixed within the optical path so that the mirror surface is situated on the ocular axes OL and OR. In this case, the objective ocular refractivity measuring optical system 19 is arranged to be movable horizontally in the direction of the left and right eyes.

If objective ocular refractivity measurement is performed in advance and the measured values are utilized, that is, if a subjective ocular refractivity measurement is performed using lenses for subjective measurement corresponding to the measured values, it is possible to shorten the measuring time for subjective ocular refractivity measurement. Furthermore, if the objective ocular refractivity measuring system 19 is provided with a display means 19a, such as a television monitor or the like, and the distance between the pupils is measured by detecting the amount of movement of the dichroic mirror 18a and/or the objective ocular refractivity measuring optical system 19 by a known moving amount detection means 20, such as an encoder or the like, when aligning images of respective anterior portions of the left and right eyes by imaging the images, the turret 17 can be easily positioned.

If the collimating lens 12 is retracted away from the ocular axis of the eyes ER and EL, the visual target 13 may also be used as a visual target for near sight. In such a case, however, it is necessary to obliquely dispose the lenses 11L and 11R for subjective measurement relative to the ocular axes OL and OR.

Figure 7:
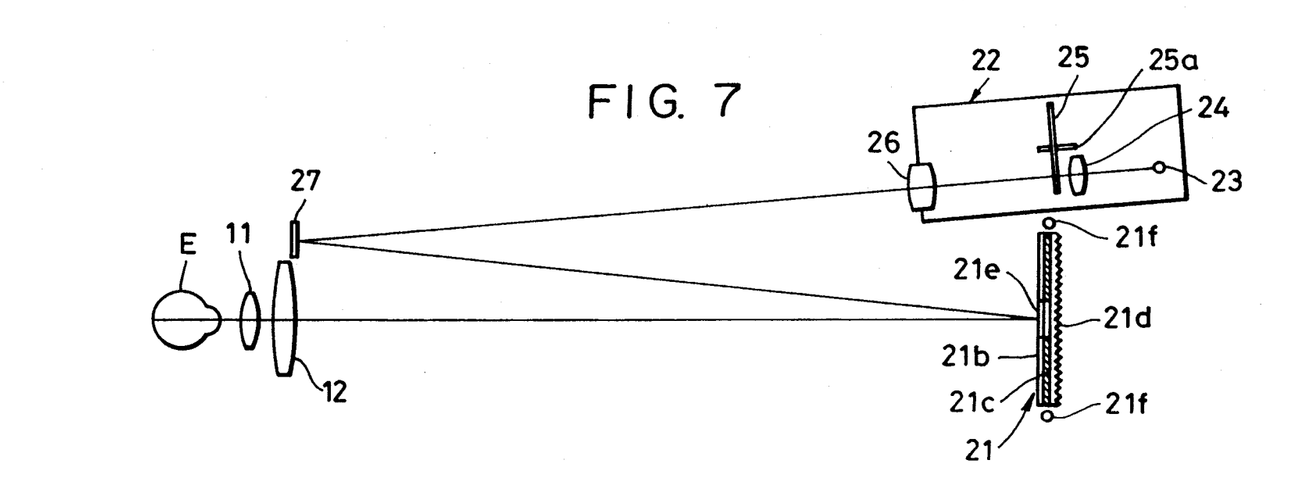
FIG. 7 is a schematic side view illustrating still another embodiment of the present invention which uses different illuminating systems.
Figure 8:
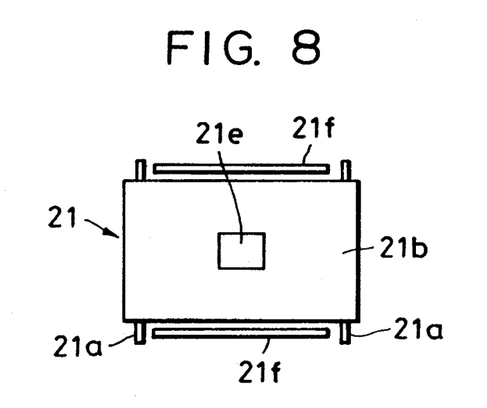
FIG. 8 is a front view of a visual target unit.
Figure 9:
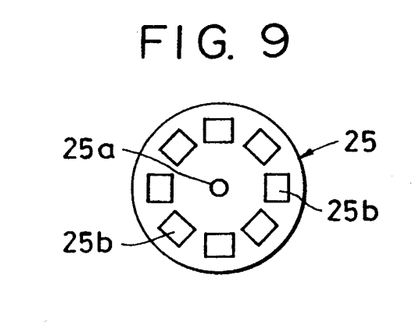
FIG. 9 is a front view illustrating a turret for holding visual targets.

FIG. 7 illustrates still another embodiment of the present invention which uses different illuminating systems. In FIG. 7, the lens 11 for subjective measurement shown in FIG. 4 is disposed in front of each eye E to be tested. The collimating lens 12 shown in FIG. 4, having a diameter greater than the distance between the pupils and common to the two eyes E, is disposed in front of the lens 11. A visual target unit 21 is disposed at or near the position of the focus of the collimating lens 12. As shown in the front view of FIG. 8, the visual target unit 21 comprises a film 21b stretched in a state wound around two rolls 21a provided at the right and left sides of the visual target unit 21 at the side of the eyes E. A diffusive plate 21c, and an acrylic plate 21d having projections and recesses at its back surface are provided at the back of the film 21b. A central portion of the diffusive plate 21c serves as a reflective screen portion 21e. Only the portion of the film 21b corresponding to the screen portion 21e is transparent. By winding many kinds of films 21b around the rolls 21a, a film suitable for a person to be tested may be selected. Rod-like light sources 21f each having nearly the same length as the lateral width of the film 21b are provided above and below the acrylic plate 21d. A visual target projection unit 22 is provided above the visual target unit 21. A light source 23, a condenser lens 24, a turret 25 and a projection lens 26 are disposed within the visual target projection unit 22. Light beams projecting from the visual target projection unit 22 are projected on the visual target unit 21 via a mirror 27. As shown in FIG. 9, the turret 25 is a disk rotatable around a shaft 25a, and includes, for example, 8 kinds of visual targets 25b on its circumference. One of the visual targets 25b can be selectively disposed within the optical path of the visual target projection unit 22.

When providing the eye E with a visual target, if the light sources 23 and 21f are lit, light beams from the light source 23 pass through the condenser lens 24, the turret 25, and the projection lens 26 to the mirror 27, are reflected by the mirror 27 to the screen portion 21e of the visual target unit 21, and are reflected by the screen portion 21e to pass through the collimating lens 12 and the lens 11 to the eye E to provide the eye E with the selected target 25b. Light beams from the light sources 21f are incident on the upper and lower sides of the acrylic plate 21d, and are diffused by repeated total reflection at the projections and recesses at the back surface thereof, illuminating nearly uniformly the diffusive plate 21c and the film 21b from behind. Hence, the light beams can also illuminate the target 25b to the same degree.

In the ocular refractivity measuring apparatuses according to the embodiments shown in FIGS. 4 and 7, the visual target is disposed at or near the position of the focus of a collimating lens having a diameter greater than the distance between the pupils of the eyes to be tested, the eyes are provided with the visual target via the collimating lens and the lenses for measuring refractivity separately provided before the respective eyes, and the ocular refractivity is measured by changing the diopter values of the lenses for measuring ocular refractivity. Hence, it is possible to dispose the visual target near the eyes to be tested and therefore to reduce the space required for such measurement. Furthermore, the field of view is not restricted during measurement, thereby producing a natural visual sensation; the visual target can be seen in the same manner even if the pupil distance changes, and therefore, an ocular refractivity measurement can be performed in a stable state. Hence, accuracy in measurement is high.

Figure 10:
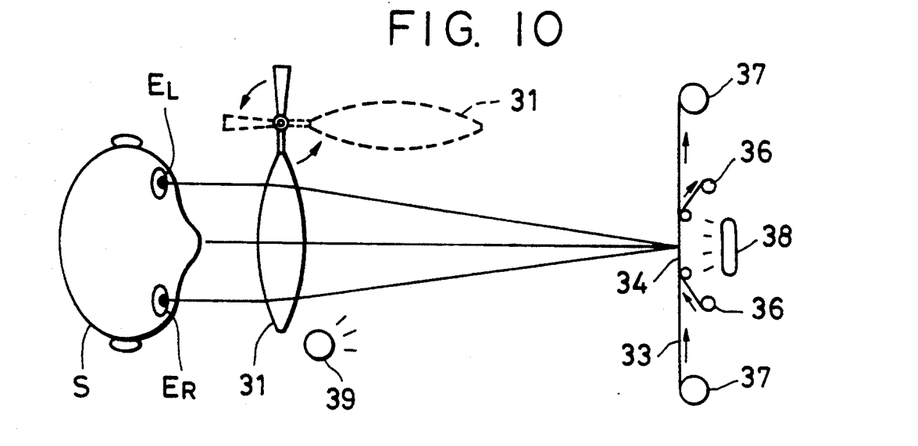
FIG. 10 is a schematic top view illustrating still another embodiment of the present invention which uses a distant-scene image for a surrounding portion of the visual target.

FIG. 10 illustrates still another embodiment of the present invention which uses a distant-scene image for a portion surrounding a target portion of a target. A person S to be tested performs subjective optometry by looking at a photograph 33 including a visual target 34 provided near or at the focal point of a lens 31, through the lens 31. Since light beams from respective points on the visual target 34 become parallel light beams as they enter the eyes to be tested, the view does not change even if the eyes move back and forth, or to the right and left.

Figure 11A:
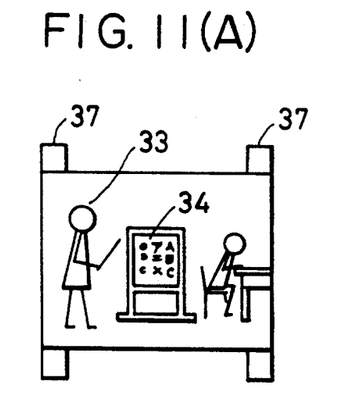
FIGS. 11(A) and 11(B) are front views showing specific examples of visual targets.

As shown in FIG. 11(A), photograph 33 also includes a surrounding field of view comprising a photograph of an optometric room or the like as a far-sight image provided in the neighborhood of the visual target 34. The photograph can be seen in the most natural state without eye strain if the apparent visual angle from which the person in the photograph is viewed by person S to be tested, is adjusted to be the visual angle from which the person in the photograph would be seen if the person in the photograph was actually standing 5–6 m from the person S to be tested.

Figure 11B:
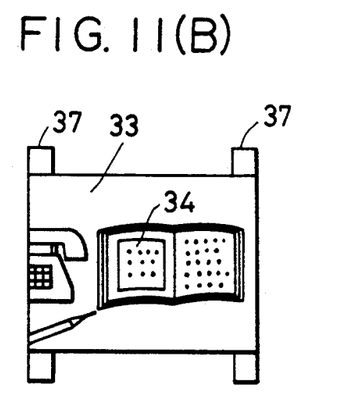

In near-sight inspection, if the lens 31 is retracted to a position out of the optical path from the eyes EL, ER to the target 34 as shown by broken lines, the visual target 34 is directly seen. At that time, by moving winding rolls 37, the surrounding field of the photograph 33 is replaced with a near-sight image as shown in FIG. 11(B). This photograph 33 includes an object which is seen to be the same size as the visual target 34 when seen from a distance of 30–40 cm. In the embodiments shown in FIGS. 10, 11(A), and 11(B), photograph 33 is wound on the moving winding rolls 37. The photograph 33 includes the visual target 34 and the surrounding field of view. As shown in FIG. 11(B), for near sight inspection, it is preferable for target 34 to be a picture of an object with which the person S is familiar. The size of the picture of the object should be such that when the picture is held at a distance of 30–40 cm from the person S, the picture of the object appears to be same size as the object itself when the object itself is positioned 30–40 cm from the person S.

In FIG. 10, the visual target 34 may also be changed in various ways, such as for distant sight, near sight and the like, by moving winding rolls 36. The visual target 34 is illuminated by a light source 38 from behind, and the entire assembly including the surrounding portion is illuminated by a light source 39.

It is convenient if the focal length of the lens 31 equals the distance for near-sight inspection. If diameter of the lens 31 is greater than the distance between the pupils of the eyes, nothing hinders the field of view. Hence, it is possible to provide a field of view of 40°–50°. A distant-sight sensation is provided due to this wide field of view and a distant-scene image, preventing mechanical myopia.

In the present embodiment, the visual target and the surrounding scene are separated from each other. However, when various kinds of visual targets are not used, one image may be used with its central portion being a visual target and its surrounding portion being a surrounding scene.

Figure 12A:
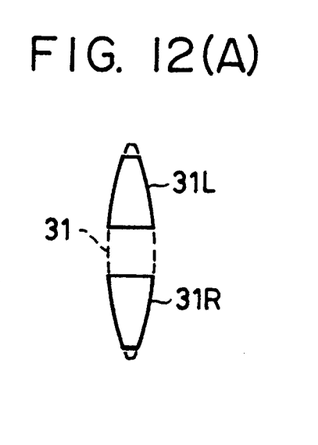
FIGS. 12(A) and 12(B) are side and front views, respectively, illustrating still another embodiment of the present invention which uses a collimating lens which does not have a lens portion on its optical axis.
Figure 12B:
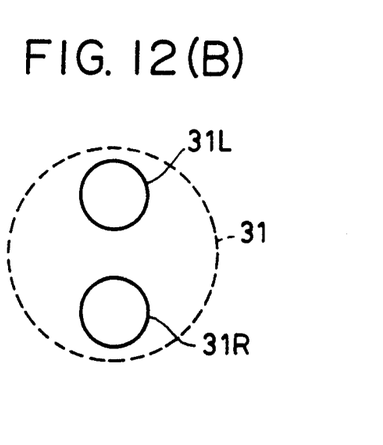

FIGS. 12(A) and 12(B) illustrate still another embodiment of the present invention which uses a collimating lens which has no lens portion on its optical axis. Although the same optometric apparatus as shown in FIG. 1 will be explained in the following description, the present embodiment may also be applied to all the ocular refractivity measuring apparatuses shown in FIGS. 4, 6 and 7.

In FIGS. 12(A) and 12(B), lens portions 31L and 31R, separated for left and right eyes, constitute a lens 31. When eyes to be tested are sufficiently close to the lens portions 31L and 31R, the field of view is not restricted even is such separated lens portions are used. The lens portions 31L and 31R are cut from the lens 31 as shown in FIG. 12(B), and are arranged so as to constitute part of the lens 31 as shown in FIG. 12(A).

Figure 13:
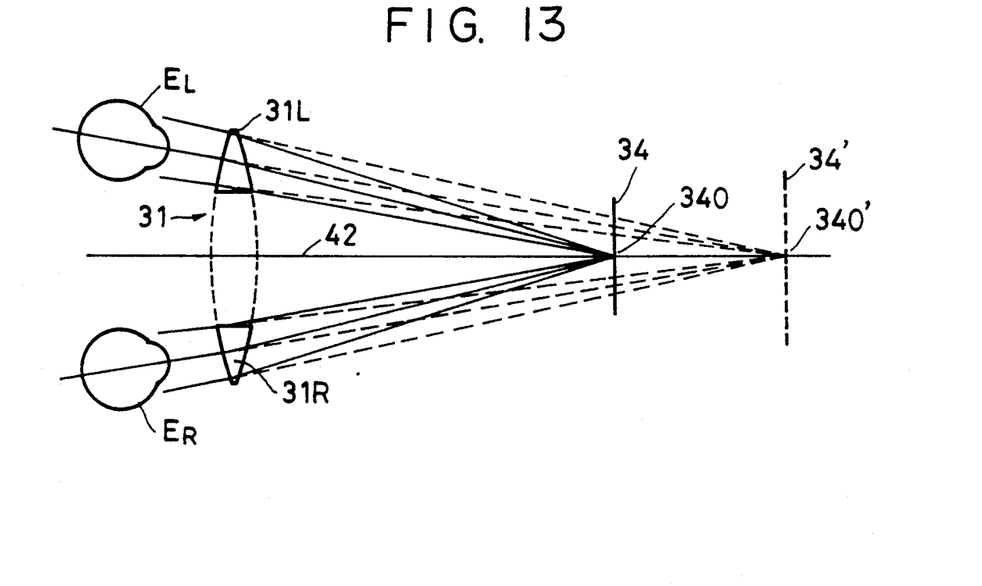
FIG. 13 is a schematic side view illustrating a state of looking at a neighborhood via the lens shown in FIG. 12(A) and 12(B)

FIG. 13 illustrates a state of viewing a neighborhood through the lens 31 shown in FIGS. 12(A) and 12(B).

When eyes $E_R$ and $E_L$ to be tested look at a near visual target 340 through the lens portions 31R and 31L of the lens 31, a virtual image 340' is produced at a predetermined apparent distance (30–40 cm from the eyes). Light beams from the visual target 340 on the optical axis 42 of the lens 31 reach the eyes as if they came from the apparent point 340'. The plane of the virtual image 34' is perpendicular to the optical axis 42, as is the plane of the visual target 34. Hence, image surfaces seen from the left and right eyes $E_L$ and $E_R$ become identical, and distortion in images is not produced. As for convergence, the situation is the same as when an object is placed in place of the image 34' and is seen without using the lens.

Figure 14:
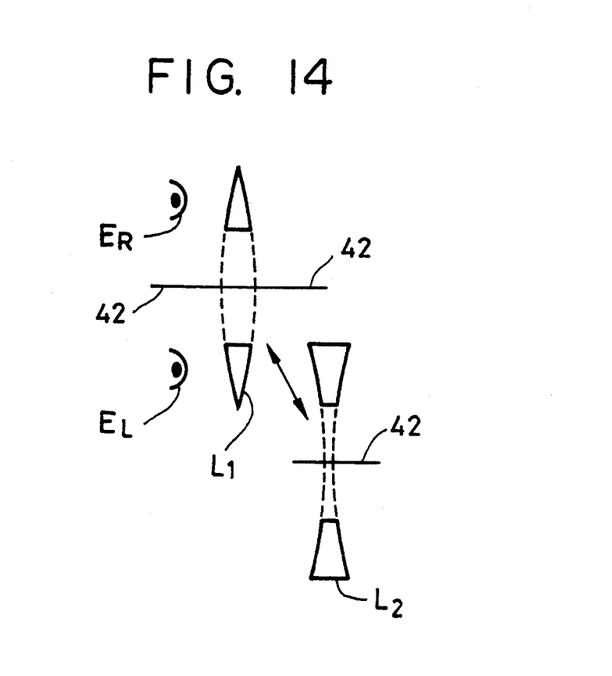
FIGS. 14 and 15 are schematic side views showing how power is changed by using different lenses.
Figure 15:
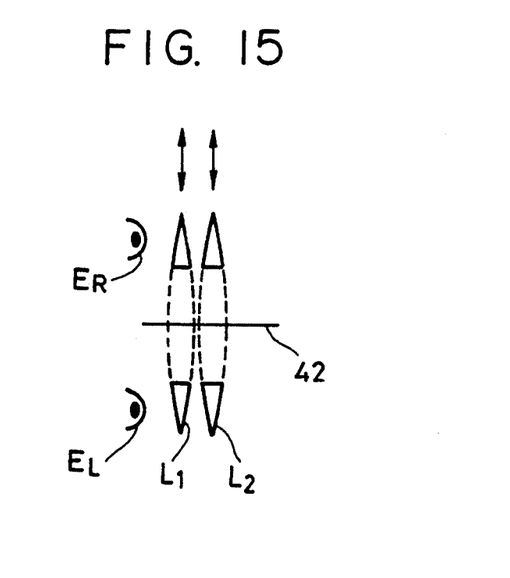

If it is desired to change the apparent distance of the visual target 34, the lens 31 may be replaced with a lens $L_1$ or $L_2$ having a different power as shown in FIG. 14, or another lens having the common optical axis may be added as shown in FIG. 15, so that two lenses $L_1$ and $L_2$ are provided. In such cases, either a convex lens or a concave lens may be used. In FIGS. 14 and 15, both lenses $L_1$ and $L_2$ have an optical axis 42 and they may be disposed within the optical path from the eyes to the target or retracted out of the optical path. Alternatively, the lenses $L_1$ and $L_2$ may have different focal lengths, one of the lenses may be fixed within the optical path, and the other lens may be disposed within the optical path or retracted out of the optical path. If it is necessary to test a single eye, each eye may be alternately shielded by a shutter.

Figure 16:
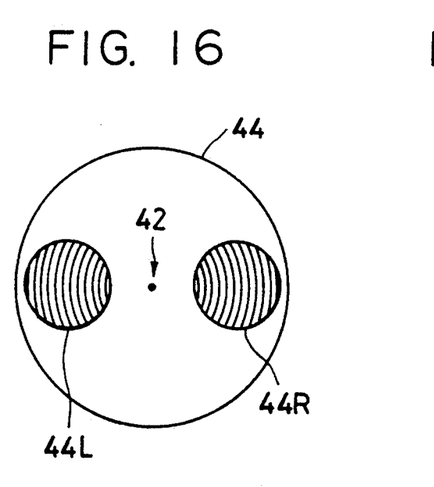
FIG. 16 is a schematic front view illustrating still another embodiment of the present invention which uses Fresnel lenses.

FIG. 16 illustrates still another embodiment of the present invention which uses lenses of another type. In FIG. 16, liquid-crystal lenses 44L and 44R are Fresnel lenses which are part of a large lens 44 having an optical axis 42.

Figure 17:
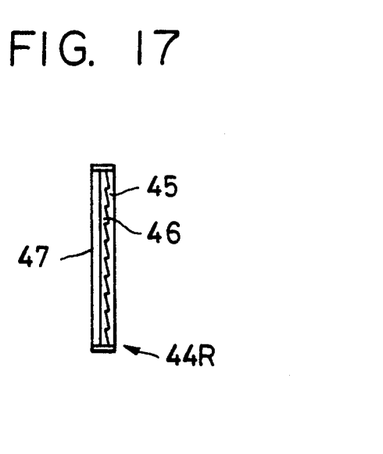
FIG. 17 is a cross-sectional view of the lens shown in FIG. 16.

FIG. 17 is a cross-sectional view of the liquid crystal lens. A liquid crystal is injected between an eccentric Fresnel lens 45 and a cover glass 47. Electrodes at both sides control the molecules of the liquid crystal to change the refractive index and thereby change the focal length. If the lenses 44R and 44L are used in place of the lenses 31R and 31L, it is possible to perform optometry with various apparent distances. If the focal length is changed before the eyes, the apparent visual angle of the visual target does not change. Hence, no inconvenience occurs.

According to the above-described embodiments, the view within the field of view does not change even if the position of eyes or the position of a face is moved, and a central visual target looks as if it were at a far distance due to a wide distant-scene field of view. Hence, no mechanical myopia is produced. Furthermore, correct subjective ocular refractivity measurement and optometric measurement can be performed in a small space.

The lenses, the light sources, and the objective ocular refractivity measuring optical system shown in the drawings are well known in the optic and ophthalmic device art and their specific construction and operation is not critical to the invention or the best mode for carrying out the invention. Therefore, no further description is necessary.

What is claimed is:

1. An eye examination apparatus comprising:
   a lens, having a diameter greater than the distance between the pupils of the eyes of a user to be tested, adapted to be disposed at a first position in front of the eyes;
   a first wide visual target, comprising a visual target portion and a surrounding field of view defining portion, disposed at or near a focal plane of said lens; and
   illumination means for illuminating said visual target portion and said surrounding field of view defining portion.

2. The eye examination apparatus recited in claim 1, wherein said lens has an optical power such that said visual target means appears to be 5-6 meters or more from the user.

3. The eye examination apparatus recited in claim 1, wherein said first visual target is fixed in the direction of the optical axis of said lens.

4. The eye examination apparatus recited in claim 1, wherein said lens has an optical axis and comprises lens portions spaced from the optical axis.

5. The eye examination apparatus recited in claim 1, wherein said surrounding field of view defining portion has a distant scene image thereon appearing to be approximately the same distance from the user as said visual target portion.

6. The ophthalmic apparatus recited in claim 1, wherein said illumination means comprises different light sources for illuminating said visual target portion and said surrounding field of view defining portion.

7. The eye examination apparatus recited in claim 1, wherein said lens comprises a plurality of lens elements, and wherein said apparatus further comprises:
   means for retracting at least one of said plurality of lens elements away from the first position to a second position out of the optical path of an eye of the user while said first visual target is disposed at or near the focal plane of said at least one of said plurality of lens elements defined when said at least one of said plurality of lenses is in said first position, thereby permitting the performing of a near sight test of the eyes of the user.

8. The eye examination apparatus recited in claim 7, wherein said retracting means retracts another lens element, different from said at least one of said plurality of lens elements, away from the first position to a second position out of the optical path of an eye of the user while said first visual target is disposed at or near the focal plane of said another lens element defined when said another lens element is in said first position, thereby permitting the performing of another near sight test of the eyes of the user.

9. The eye examination apparatus recited in claim 7, wherein said first visual target is adapted to be removed from its position at or near a focal plane of said lens element when said lens element is disposed in front of the eyes of the user in the optical path thereof, wherein said apparatus further comprises a second wide visual target adapted to be disposed at or near a focal plane of said lens element to be used in the near sight test of the eyes of the user when said lens element is retracted to said second position by said retracting means, wherein said first and second visual targets have different kind of surrounding field.

10. An eye examination apparatus comprising:
    a single lens, having a diameter greater than the distance between the pupils of the eyes of a user to be tested, adapted to be disposed at a first position in front of the eyes;
    a first wide visual target, comprising a visual target portion and a surrounding field of view defining portion, disposed at or near a focal plane of said lens;
    illumination means for illuminating said visual target portion and said surrounding field of view defining portion; and means for retracting said lens away from the first position to a second position out of the optical path of an eye of the user while said first visual target is disposed at or near the focal plane of said lens defined when said lens is in said first position, thereby permitting the performing of a near sight test of the eyes of the user.

11. The ophthalmic apparatus recited in claim 10, wherein said first visual target is adapted to be removed from its position at or near a focal plane of said lens when said lens is disposed in front of the eyes of the user in the optical path thereof, wherein said apparatus further comprises a second wide visual target adapted to be disposed at or near a focal plane of said lens to be used in the near sight test of the eyes of the user when said lens is retracted to said second position, wherein said first and second visual targets have different kind of surrounding field.

12. An ophthalmic apparatus comprising:
two variable-diopter subjective ocular refractivity measuring lenses spaced apart and adapted to be disposed in front of the right and left eyes of a user to be tested;
a lens, having a diameter greater than the distance between the pupils of the eyes of the user to be tested, adapted to be disposed at a first position in front of the two variable-diopter subjective ocular refractivity measuring lenses;
a first wide visual target, comprising a visual target portion and a surrounding field of view defining portion, disposed at or near a focal plane of said lens; and
illumination means for illuminating said visual target portion and said surrounding field of view defining portion.

13. The ophthalmic apparatus recited in claim 12, wherein said lens has an optical power such that said visual target means appears to be 5-6 meters or more from the user.

14. The ophthalmic apparatus recited in claim 12, further comprising:
a light beam divider positioned between said two variable diopter subjective ocular refractivity measuring lenses and said lens; and
an objective ocular refractive power measuring system positioned to receive light from said light beam divider.

15. The ophthalmic apparatus recited in claim 14, wherein said objective ocular refractive power measuring system comprises display means for displaying images of the anterior portion of the user's right and left eyes.

16. The ophthalmic apparatus recited in claim 15, further comprising left-and-right eye direction moving amount detecting means for detecting the distance between the pupils of the eyes of the user according to the images of the anterior portion of the right and left eyes of the user, and wherein said two variable diopter subjective ocular refractivity measuring lenses are displaceable in a direction connecting the right and left eyes of the user in order to adjust the distance between said two variable-diopter subjective ocular refractivity measuring lenses to be equal to the distance between the pupils of the right and left eyes of the user.

17. The ophthalmic apparatus recited in claim 12, wherein said first visual target is fixed in the direction of the optical axis of said lens.

18. The ophthalmic apparatus recited in claim 12, wherein said lens has an optical axis and comprises a lens portion spaced from the optical axis.

19. The ophthalmic apparatus recited in claim 12, wherein said surrounding field of view defining portion has a distant scene image thereon appearing to be approximately the same distance from the user as said visual target portion.

20. The ophthalmic apparatus recited in claim 12, wherein said illumination means comprises different light source for illuminating said visual target portion and said surrounding field of view defining portion.

21. The ophthalmic apparatus recited in claim 12, wherein said lens comprises a single lens, and wherein said apparatus further comprises:
means for retracting said lens away from the first position to a second position out of the optical path of an eye of the user while said first visual target is disposed at or near the focal plane of said lens defined when said lens is in said first position, thereby permitting the performing of a near sight test of the eyes of the user.

22. The ophthalmic apparatus recited in claim 21, wherein said first visual target is adapted to be removed from its position at or near a focal plane of said lens when said lens is disposed in front of the eyes of the use in the optical path thereof, wherein said apparatus further comprises a second wide visual target adapted to be disposed at or near a focal plane of said lens to be used in the near sight test of the eyes of the user when said lens is retracted to said second position by said retracting means, wherein said first and second visual targets have different kind of surrounding field.

23. The ophthalmic apparatus recited in claim 12, wherein said two dipoter-value-variable subjective ocular refractivity measuring lenses are displaceable in a direction perpendicular to the optical axis thereof in order to adjust the distance between said two variable-diopter subjective ocular refractivity measuring lenses to be equal to be equal to the distance between the pupils of the right and left eyes of the user.

24. The ophthalmic apparatus recited in claim 12, wherein said lens comprises a plurality of lens elements, and wherein said apparatus further comprises:
means for retracting at least one of said plurality of lens elements away from the first position to a second position out of the optical path of an eye of the user while said first visual target is disposed at or near the focal plane of said at least one of said plurality of lens elements defined when said at least one of said plurality of lens elements is in said first position, thereby permitting the performing of a near sight test of the eyes of the user.

25. The ophthalmic apparatus recited in claim 24, wherein said retracting means retracts another lens element, different from said at least one of said plurality of lens elements, away from the first position to a second position out of the optical path of an eye of the user while said first visual target is disposed at or near the focal plane of said another lens element defined when said another lens element is in said first position, thereby permitting the performing of another near sight test of the eyes of the user.

26. The ophthalmic apparatus recited in claim 24, wherein said first visual target is adapted to be removed from its position at or near a focal plane of said lens element when said lens element is disposed in front of the eyes of the user in the optical path thereof, wherein said apparatus further comprises a second wide visual target adapted to be disposed at or near a focal plane of said lens element to be used in the near sight test of the eyes of the user when said lens element is retracted to said second position by said retracting means, wherein said first and second visual targets have different kind of surrounding field.

* * * * *

UNITED STATES PATENT AND TRADEMARK OFFICE
CERTIFICATE OF CORRECTION

| | |
|---|---|
| PATENT NO. : | 5,231,430 |
| DATED : | JULY 27, 1993 |
| INVENTOR(S) : | YOSHIMI KOHAYAKAWA |

It is certified that error appears in the above-identified patent and that said Letters Patent is hereby corrected as shown below:

COLUMN 3
    Line 67, "din" should read --in--.

COLUMN 6
    Line 19, "abberation" should read --aberration--; and
    Line 59, "use" should read --used--.

COLUMN 13
    Line 8, "ophthalmic" should read --eye examination--.

COLUMN 14
    Line 20, "use" should read --user--; and
    Line 35, "to be equal" should be deleted.

Signed and Sealed this

Nineteenth Day of April, 1994

Attest:

BRUCE LEHMAN

*Attesting Officer*     *Commissioner of Patents and Trademarks*